United States Patent
Bödiger et al.

(10) Patent No.: US 6,774,268 B2
(45) Date of Patent: Aug. 10, 2004

(54) SUBSTANCE MIXTURE CONTAINING BISPHENOL A

(75) Inventors: Michael Bödiger, League City, TX (US); Rainer Neumann, Krefeld (DE); Frieder Heydenreich, Düsseldorf (DE); Michael Prein, Brasschaat (BE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/240,054

(22) PCT Filed: Mar. 19, 2001

(86) PCT No.: PCT/EP01/03114

§ 371 (c)(1),
(2), (4) Date: Sep. 26, 2002

(87) PCT Pub. No.: WO01/74750

PCT Pub. Date: Oct. 11, 2001

(65) Prior Publication Data

US 2003/0096939 A1 May 22, 2003

(30) Foreign Application Priority Data

Mar. 30, 2000 (DE) .......................................... 100 15 864

(51) Int. Cl.⁷ ............................................... C07C 39/16
(52) U.S. Cl. ...................................................... 568/728
(58) Field of Search ......................................... 568/728

(56) References Cited

U.S. PATENT DOCUMENTS

| | | | |
|---|---|---|---|
| 2,775,620 A | | 12/1956 | Williamson ................. 260/619 |
| 4,209,646 A | * | 6/1980 | Gac |
| 4,260,704 A | * | 4/1981 | Schmidt |
| 4,859,803 A | | 8/1989 | Shaw ......................... 568/727 |
| 4,954,661 A | * | 9/1990 | Iimuro |
| 5,786,522 A | * | 7/1998 | Cipullo |

FOREIGN PATENT DOCUMENTS

| | | |
|---|---|---|
| EP | 0 552 518 | 7/1993 |
| EP | 0 758 637 | 2/1997 |
| EP | 0 812 815 | 12/1997 |

* cited by examiner

Primary Examiner—Michael L. Shippen
(74) Attorney, Agent, or Firm—Joseph C. Gil; James R. Franks; John E. Mrozinski, Jr.

(57) ABSTRACT

The present invention provides mixtures containing bisphenol A, methods for the production thereof. The mixtures of the present invention may find use in the production of polymeric materials.

5 Claims, 1 Drawing Sheet

SUBSTANCE MIXTURE CONTAINING BISPHENOL A

FIELD OF THE INVENTION

The present invention relates to mixtures of substances containing bisphenol A as well as two processes for the preparation thereof and their use for preparing polymer materials.

BACKGROUND OF THE INVENTION

Bis(4-hydroxyaryl)alkanes, in the following called bisphenols, are important as starting materials or as intermediates for preparing a number of commercial products. Bisphenols can be prepared by the condensation of phenols and carbonyl compounds. Substituted phenols or unsubstituted phenol may be used.

The condensation product from the reaction between phenol and acetone, 2,2-bis(4 hydroxyphenyl)propane (bisphenol A, BPA, p,p-BPA) is of particular industrial importance. BPA is used as a starting material for preparing various types of polymer materials such as, for example, polyarylates, polyetherimides, polysulfones and modified phenol/formaldehyde resins. Preferred areas of application are the preparation of epoxy resins and polycarbonates.

Processes for preparing bisphenols by acid-catalysed reaction of phenols with carbonyl compounds are known, for example from U.S. Pat. No. 2,775,620 and from EP-A-0 342 758.

Bisphenols of general structure can be prepared by processes which are analogous to the preparation of BPA.

Phenol resins are artificial resins which are obtained by the condensation of phenols (or bisphenol A) with aldehydes, in particular formaldehyde, by derivatisation of the condensates resulting therefrom or by the addition of phenols to unsaturated compounds such as e.g. acetylene, terpenes or natural resins.

Compounds called epoxide resins are either oligomeric compounds with more than one epoxide group per mole, which are used to prepare thermoset materials, or else the corresponding thermoset materials themselves. The conversion of epoxide resins is achieved via polyaddition reactions with suitable hardeners or by polymerisation via the epoxide group. More than 90% of current world-wide production takes place by reacting bisphenol A with epichlorhydrin.

The term formaldehyde resins includes the industrially very important urea, melamine, phenol and, in a wider sense, furan resins which are prepared by condensation of formaldehyde with urea, melamine, phenol or phenols (including bisphenol A) and furfuryl alcohol as monomers which contain NH or OH groups.

Polymer materials such as, for example, phenol resins, epoxide resins or formaldehyde resins may be prepared using bisphenol A as a raw material. The disadvantage of this is that bisphenol A in the pure form is expensive, and in addition it is disadvantageous that the properties of the polymer materials mentioned are not optimal when they are prepared using pure bisphenol A as a raw material.

SUMMARY OF THE INVENTION

Thus, the present invention is based on the object of providing a process for preparing polymer materials, for example phenol resins, epoxide resins or formaldehyde resins, which does not have the disadvantages of the prior art mentioned above.

The object according to the invention is the use of a mixture of substances containing bisphenol A and secondary products which are produced during the production of bisphenol A to prepare polymer materials such as, for example, phenol resins, epoxide resins or formaldehyde resins.

The present invention therefore provides a mixture of substances containing bisphenol A and secondary products which are produced during the production of bisphenol A.

DETAILED DESCRIPTION OF THE INVENTION

Figure 1:
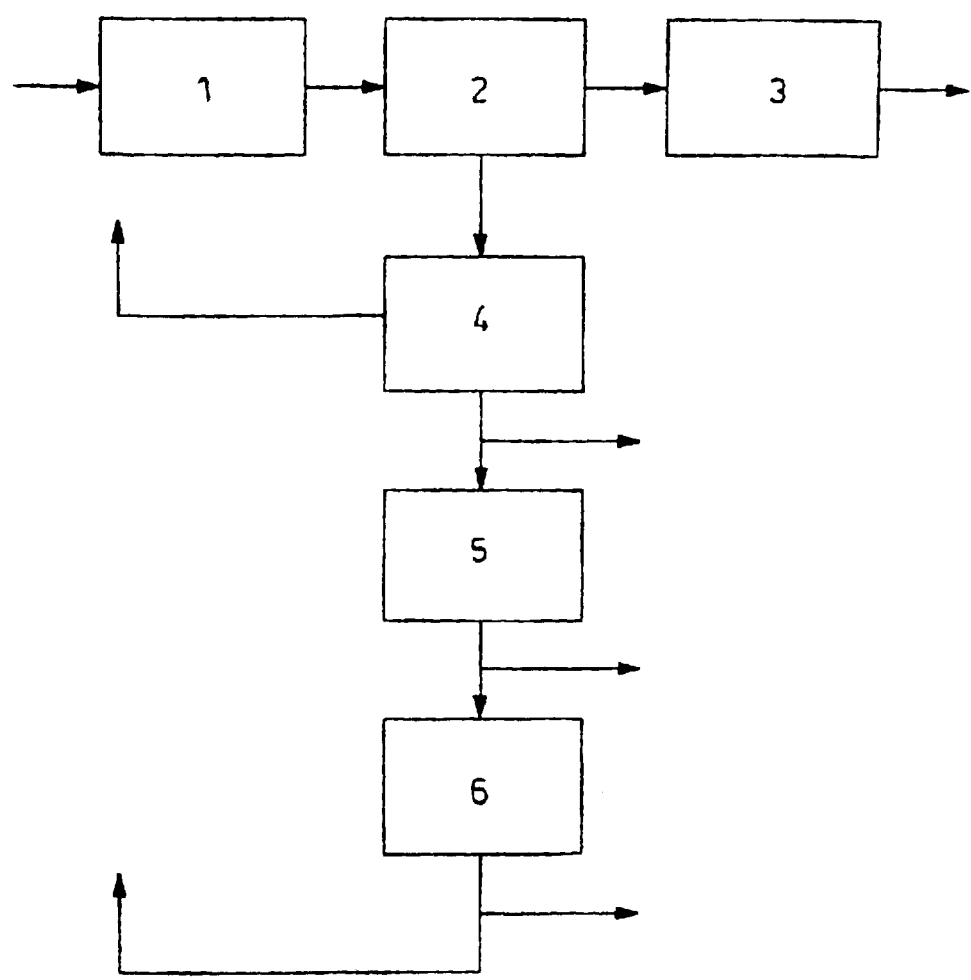
FIG. 1 is a schematic representation of the process according to the present invention.

The mixture of substances according to the invention contains (data in wt. %):
p,p-BPA: 35 to 75, preferably 40 to 65
o,p-BPA: 5 to 25, preferably 10 to 20
sum of bisphenols (p,p-BPA+o,p-BPA): 50 to 80, preferably 60 to 70
secondary products which are produced during the production of bisphenol A: 50 to 20, preferably 40 to 30.

The sum of the proportions by weight of p,p-BPA and o,p-BPA and the secondary products is 100 wt. %.

Secondary products which are produced during the production of bisphenol A are, according to the invention, isomers of para,para-bisphenol A, chromanes, indanes, phenols, higher condensates of the substances mentioned, and also other compounds the structure of which is not explained in detail.

The mixture of substances according to the invention may also contain between 0 and 90 wt. %, preferably 0 to 60 wt. %, very particularly preferably 0 to 50 wt. % of phenol, with respect to the total weight of the mixture being produced therewith.

A composition differing from the composition according to the invention is a disadvantage when preparing e.g. phenol resins. If, for example, the proportion of the highly reactive component phenol is increased to more than 60 wt. %, then the rate of reaction in the common processes for preparing e.g. sheets based on thermosetting resins is too high. The mixture according to the invention exhibits advantages, as compared with pure phenol, in controlling the rate of reaction and the structure of the polymer by targeted introduction of cross-linking and branching sites.

The present invention also provides use of the mixtures of substances mentioned for preparing polymer materials, for example phenol resins, epoxide resins or formaldehyde resins.

The present invention also provides three different processes for preparing the mixtures of substances according to the invention, which are described in the following three paragraphs:

A process for preparing the mixture of substances according to the invention, wherein in the process for preparing bisphenol A, a substream is taken from the mother liquor produced during crystallisation and filtration, after dewatering, and this is preferably rendered inert, preferably after separation of any phenol which is still present, and then put into containers.

A process for preparing the mixture of substances according to the invention, wherein in the process for preparing bisphenol A, a substream is taken from the mother liquor obtained during crystallisation and filtration, after dewatering, and this is supplied to a rearrangement reaction at temperatures between 50° C. and 90° C. with residence times of 2 to 12 hours on an acid ion-exchanger (some of the secondary products are then rearranged to give p,p-bisphenol A) and a substream is taken from this rearranged product which is rendered inert, preferably after separation of any phenol still present, and then put into containers.

A process for preparing a mixture of substances according to the invention, wherein in the process for preparing bisphenol A, a substream is taken from the mother liquor obtained during crystallisation and filtration, after dewatering, and this is then preferably supplied to a rearrangement reaction at temperatures between 50 and 90° C. with residence times of 2 to 12 hours on an acid ion-exchanger (some of the secondary products are then rearranged to give p,p'-bisphenol A) and is then concentrated by distillation, a crystalline bisphenol A phenol adduct is then extracted from this by crystallisation at a temperature of 40 to 50° C. with a residence time of 1 to 6 hours and isolated by filtration and the remaining liquid mixture, preferably after separation of any phenol still present, is rendered inert and then put into containers.

The present invention has many advantages; in particular, mixtures of substances according to the invention are of high quality and have good storage stability. They are used as raw materials for preparing high quality polymer materials such as, for example, phenol resins, epoxide resins or formaldehyde resins.

Mixtures of substances according to the invention are preferably diluted with phenol, when the phenol used is preferably acid-free, alkali-free and metal-free.

Mixtures of substances according to the invention are preferably prepared under inert conditions, i.e. in particular with the exclusion of oxygen.

Mixtures of substances according to the invention have advantages, as compared with pure bisphenol A, as raw materials for the preparation of the polymer materials mentioned. For example, regulating the rate of polymerisation is simpler and in addition targeted cross-linking and branching sites are introduced to the polymer materials mentioned by the mixtures of substances according to the invention.

A composition for the mixture of substances which differs from the composition according to the invention is disadvantageous for the preparation of polymer materials such as, for example, phenol resins. If, for example, the proportion of the highly reactive component phenol is increased to more than 60 wt. %, in particular more than 90 wt. %, then the rate of reaction is too high in common processes for preparing products, for example sheets based on thermosetting resins. Mixtures of substances according to the invention exhibit, as compared with pure phenol, advantages in regulating the rate of reaction and the structure of the polymer by targeted introduction of cross-linking and branching points into the polymer material.

The process according to the invention for preparing BPA is preferably based on the acid-catalysed reaction of phenol with acetone, wherein a ratio by amounts of phenol:acetone of greater than 5:1 is used in the reaction. Homogeneous or heterogeneous Bronsted acids or Lewis acids are used as acid catalysts, that is, for example, strong mineral acids such as hydrochloric acid or sulfuric acid. Gel-like or macroporous sulfonated cross-linked polystyrene resins (acid ion exchangers) are preferably used. The details given below refer to a process of preparation using acid ion exchangers as catalysts.

In order to produce high selectivity, the reaction of phenol with acetone can be performed in the presence of suitable mercapto compounds as cocatalysts. These may either be dissolved homogeneously in the reaction solution or be fixed to the sulfonated polystyrene matrix via ionic or covalent bonds. The reaction unit is preferably a fixed layer bed or a fluidised bed which is traversed upwards or downwards or a column of the reactive distillation column type.

During the reaction of phenol with acetone in the presence of acid catalysts and mercapto compounds as cocatalysts, a product mixture is produced which contains, in addition to unreacted phenol and optionally acetone, primarily BPA and water. In addition, there are also small amounts of typical secondary products of the condensation reaction such as, for example, 2-(4-hydroxyphenyl)-2-(2-hydroxyphenyl) propane (o,p-BPA), substituted indenes, hydroxyphenyl indanoles, hydroxyphenyl chromanes, substituted xanthenes and higher condensed compounds with three or more phenyl rings in the molecular structure.

The secondary products mentioned, as well as water, phenol and acetone, may impair the suitability of BPA for preparing polymers and have to be separated by suitable methods. High specifications relating to purity are generally required for the raw material BPA, in particular when preparing polycarbonate.

The working up and purification of BPA is normally performed by means of a multistage cascade of suitable purification processes such as, for example, suspension crystallisation, melt crystallisation, distillation and desorption. In an industrially preferred embodiment, BPA is isolated from the reaction mixture in the form of an approximately equimolar crystalline adduct with phenol by cooling the reaction mixture, when the BPA/phenol adduct crystallises out. The crystallisation process is preferably performed as a suspension crystallisation. Suspension crystallisation is understood to be crystallisation from a liquid due to cooling, wherein the crystals form a suspension with the liquid (solid/liquid). The BPA/phenol adduct crystals are then separated from the liquid phase, using equipment suitable for solid/liquid separation such as a rotary filter or a centrifuge, and if required taken on for further purification. Thus, adduct crystals are obtained which typically have a purity greater than 99 wt. % of BPA, with respect to the secondary components, with a phenol content of about 40 wt. %. Impurities which adhere to the surface of the adduct crystals can be removed by washing with suitable solutions which typically contain one or more components from the group acetone, water, phenol, BPA and secondary components.

The stream of liquid (mother liquor) produced during solid/liquid separation contains phenol, BPA, water produced during reaction and unreacted acetone and is enriched in the secondary components typically produced during BPA preparation. In a preferred embodiment, this mother liquor is recycled to the reaction unit. In order to maintain the catalytic activity of the acid ion exchanger any water produced is preferably removed by distillation, wherein any acetone still present is also optionally removed from the mother liquor. The dewatered reaction stream obtained in this way is topped up with phenol and acetone and returned to the reaction unit. Alternatively, water and acetone may also be partly or entirely removed by distillation prior to performing suspension crystallisation of the BPA/phenol adduct. During the distillation steps described above, some of the phenol present in the reaction solution may also be removed by distillation.

In the case of this type of circulation procedure the problem is that secondary products from the preparation of BPA accumulate in the circulation stream and can lead to deactivation of the catalyst system. In order to avoid excessive accumulation of secondary components in the circulation stream, some of the circulation stream, optionally after partial or complete recovery of phenol by distillation, is excluded from the process chain as a BPA resin.

In addition, it has proven advantageous to pass some or the entire amount of the circulation stream, after solid/liquid separation and before or after the removal of water and residual acetone, over a rearrangement unit filled with acid ion exchanger. This unit is generally operated at a higher temperature than the reaction unit. In this rearrangement unit, under the conditions present therein, some of the secondary components from BPA preparation and present in the circulation stream are isomerised to give BPA, so that the overall yield of BPA can be increased.

The BPA/phenol adduct crystals obtained after the completion of suspension crystallisation of the reaction solution and solid/liquid separation as described above are then taken, if required, to further purification stages, wherein the isolation of phenol and optionally a reduction in the concentration of secondary components is achieved.

Thus, the adduct crystals can be recrystallised, for example, from phenol, from organic solvents, from water or from mixtures of the compounds mentioned in accordance with a suspension crystallisation procedure. The phenol present in the adduct crystals can also be entirely or partly removed by choosing a suitable solvent. The phenol optionally remaining in the BPA after recrystallisation can then be entirely removed by suitable distillation, desorption or extraction procedures.

Alternatively, phenol can also be removed first from the adduct crystals. Preferred methods for this are desorption of the melt using hot inert gases, vacuum distillation or a combination of the methods mentioned. In this way, it is possible to obtain BPA with a residual phenol concentration of less than 100 ppm from the adduct crystals. By means of suitable reaction management and optionally the addition of stabilisers, it can be ensured that BPA does not decompose to a marked extent under the thermal stresses experienced during the removal of phenol by distillation or desorption.

Depending on the process conditions for suspension crystallisation from the reaction solution and when performing the solid/liquid separation and crystal washing, the BPA obtained is suitable for preparing polymer materials after the removal of phenol from the adduct crystals. It may be necessary to take the BPA obtained after the removal of phenol to a further purification operation, in particular in order to prepare high quality materials such as polycarbonates. Final purification may be performed by suspension crystallisation from water or suitable organic solvents, melt crystallisation in the form of a static or dynamic layer crystallisation, extraction with water, aqueous neutral, acid or basic salt solutions or suitable organic solvents or in the form of a single-stage or multi-stage distillation. It is possible to obtain BPA with a purity of greater than 99.9 wt. % by performing the purification operations mentioned, or a suitable combination thereof, this BPA being especially suitable for preparing high quality polymer materials.

A preferred embodiment of the present invention is characterised in that, after dewatering, a substream is taken from the mother liquor produced during crystallisation and filtration in the process described for preparing bisphenol A. This substream preferably corresponds to 5 to 15 wt. % of the mother liquor produced. This substream preferably contains less than 0.5 wt. % of water and preferably less than 0.1 wt. % of acetone. To prepare the mixture of substances according to the invention, the substream mentioned above is preferably filtered, traces of acid are preferably completely removed therefrom, then in any case the mixture is rendered inert and put, at temperatures of preferably 60 to 100° C., into containers which are preferably made of stainless steel.

Another preferred embodiment of the present invention is characterised in that a substream produced by the process according to the preceding paragraph is isomerised at temperatures of preferably 50 to 70° C., in particular 60 to 70° C., particularly preferably 65° C., on an acid ion exchanger. Isomerisable constituents, for example o,p-bisphenol A, are thus isomerised to p,p-bisphenol A. The residence time in the isomerisation reactor is preferably 2 to 12 hours, in particular 3 to 8 hours, particularly preferably 3 to 4 hours. To prepare the mixture of substances according to the invention, the substream is filtered after isomerisation, traces of acid are preferably completely removed therefrom, then in any case the mixture is rendered inert and put, at temperatures of preferably 60 to 100° C., into containers which are preferably made of stainless steel.

Another preferred embodiment of the present invention is characterised in that, after dewatering, a substream is taken from the mother liquor produced during crystallisation and filtration in the process described for preparing bisphenol A. This substream preferably corresponds to 5 to 15% of the mother liquor produced. This substream preferably contains less than 0.5 wt. % of water and less than 0.1 wt. % of acetone. The substream is then converted in a rearrangement reaction at temperatures between 50 and 90° C. with residence times of 2 to 12 hours, on an acid ion exchanger. The substream is then concentrated by distillation. In this procedure phenol is substantially removed. The phenol content after concentration is preferably less than 70 wt. %, in particular less than 60 wt. %. The mixture concentrated in this way is crystallised in a preferably 1–2 stage crystallisation at a temperature of 40 to 50° C. with a residence time of 1 to 6 hours. The crystallised bisphenol A/phenol adduct obtained in this way is isolated by filtration and taken to the main process for preparation of bisphenol A. The remaining liquid mixture, or a part thereof, optionally after further concentration, wherein more phenol is removed, is preferably filtered in order to prepare the mixture of substances according to the invention, traces of acid are preferably completely removed therefrom, then in any case the mixture is rendered inert and put, at temperatures of preferably 80 to 125° C., into containers which are preferably made of stainless steel.

Mixtures of substances according to the invention preferably contain additional phenol in a proportion of 0 to 90 wt. %, in particular 0 to 60 wt. %, particularly preferably 0 to 50 wt. %.

Drawing 1 shows, schematically, a process for preparing mixtures of substances according to the invention. The drawing represents a preferred embodiment of the invention; the scope of the invention is not restricted to the drawing.

Phenol and acetone are supplied to unit 1 and react in unit 1 to give bisphenol A.

Crystallisation of the adduct of bisphenol A and phenol takes place in unit 2. In addition, separation of the crystallised adduct takes place in unit 2. The separated adduct is taken to unit 3 in which separation and working up of the bisphenol A takes place. The remaining mother liquor is transferred from unit 2 into unit 4 in which the removal of water (dewatering) takes place. A proportion of 85 to 95 wt. % is returned to unit 1 from unit 4, along with the supply of 2 to 6 wt. % of acetone. A mixture of substances according to the invention can be isolated after unit 4. The smaller part (5 to 15 wt. %) of the dewatered mother liquor in unit 4 is taken to unit 5. Rearrangement takes place in unit 5. A mixture of substances according to the invention can be isolated after unit 5. The rearranged mother liquor in unit 5 is taken to unit 6. In unit 6, the removal of phenol and the crystallisation and isolation of bisphenol A/phenol adducts as solid take place by filtration. A mixture of substances according to the invention can be isolated after unit 6 from the remaining mother liquor, optionally after removing any phenol still present by known processes such as e.g. distillation, desorption, etc. The recovered phenol is taken from unit 6 to unit 1, along with the supply of 2 to 6 wt. % of acetone. The mixtures of substances according to the invention which are isolated after unit 4, 5 or 6, are supplied to a container filling procedure.

In the following, the invention is explained by means of examples without restricting the scope of the invention to the examples.

In the following, mixtures of substances according to the invention and their preparation are given by way of example. Preparation takes place each time in an arrangement as described in FIG. 1.

The compositions cited for the mixtures of substances according to the invention refer to several batches which were prepared from each mixture of substances. In each individual batch, the sum of all the components was 100 wt. %.

A mixture of substances according to the invention (BPG 1) was isolated after unit 4.

A mixture of substances according to the invention (BPG 2) was isolated after unit 5.

A mixture of substances according to the invention (BPG 3) was isolated after unit 6.

| BPG1 | |
| --- | --- |
| p,p-BPA | 50 to 60 wt. % |
| o,p-BPA | 10 to 20 wt. % |
| sum of bisphenols[1] | 65 to 75 wt. % |
| trisphenols | 0 to 5 wt. % |
| indanes | 0 to 10 wt. % |
| chromanes | 5 to 15 wt. % |
| residual components[2] | 30 to 2 wt. % |
| BPG2 | |
| p,p-BPA | 60 to 70 wt. % |
| o,p-BPA | 5 to 15 wt. % |
| sum of bisphenols[1] | 65 to 75 wt. % |
| trisphenols | 0 to 3 wt. % |
| indanes | 0 to 10 wt. % |
| chromanes | 5 to 15 wt. % |
| residual components[2] | 30 to 2 wt. % |
| BPG3 | |
| p,p-BPA | 35 to 45 wt. % |
| o,p-BPA | 10 to 20 wt. % |
| sum of bisphenols[1] | 55 to 65 wt. % |
| trisphenols | 0 to 5 wt. % |
| indanes | 5 to 15 wt. % |
| chromanes | 15 to 25 wt. % |
| residual components[2] | 30 to 2 wt. % |

[1] p,p-BPA + o,o-BPA
[2] All components except phenol and bisphenols (p,p-BPA + o,p-BPA + o,o-BPA). The residual components consist, for example, of various phenols, higher molecular condensates, isopropenylphenols, etc.

In the following, comparison examples are provided:

BPG4 was obtained in the same way as BPG1, but without removing acid or traces of acid. The water content of BPG4 was greater than 0.5 wt. %. After a period of more than 5 days, BPG4 which initially had a concentration of p,p-BPA of 50.2 wt. % and a concentration of residual components of 29.4 wt. %, had decomposed. After decomposition, the composition of BPG4 was 47.7 wt. % of p,p-BPA and 32.2 wt. % of residual components.

BPG5 was obtained in the same way as BPG2; the initial mixture for rearrangement was a mixture of 50.2 wt. % of p,p-BPA and 8.2 wt. % of indanes. Rearrangement was performed under unsuitable conditions at 80° C. and for 15 hours. The result was increased formation of indane and decomposition of the p,p-BPA. After rearrangement under unsuitable conditions, BPG5 had a concentration of p,p-BPA of 42.7% and an indane content of 15.0 wt. %.

BPG6 was obtained in the same way as BPG3, but inertising conditions were not applied. After a period of more than 5 days under ambient conditions, a clear deterioration in colour, expressed as the iodine colour index, was produced. The iodine colour index increased from 300 to more than 1,000. In addition, the concentration of p,p-BPA decreased due to decomposition.

The foregoing examples of the present invention are offered for the purpose of illustration and not limitation. It will be apparent to those skilled in the art that the embodiments described herein may be modified or revised in various ways without departing from the spirit and scope of the invention. The scope of the invention is to be measured by the appended claims.

What is claimed is:

1. A process of preparing an oxygen-free mixture comprising,
   (a) separating an adduct of bisphenol A and phenol from a feed stream by means of crystallization and filtration, and concurrently forming a mother liquor substream;
   (b) dewatering said mother liquor substream;
   (c) rendering said mother liquor substream free of oxygen, thereby forming said mixture; and
   (d) placing said mixture into a container,
wherein said mixture comprises,
   35 to 75 wt. % of p,p-bisphenol A,
   5 to 25 wt. % of o,p-bisphenol A, and
   20 to 50 wt. % of secondary products which are produced during the preparation of bisphenol A,
wherein the sum of the percentages by weight of p,p-bisphenol A and o,p-bisphenol A is 50 to 80 wt. % and wherein the sum of the percentages by weight of p,p-bisphenol A and o,p-bisphenol A and the secondary products totals 100 wt. %.

2. The method of claim 1 further comprising diluting said mixture with phenol to form a diluted mixture, said diluted mixture containing up to 90 percent by weight of phenol, based on the weight of said diluted mixture.

3. A process of preparing an oxygen-free mixture comprising:
   (a) separating an adduct of bisphenol A and phenol from a feed stream by means of crystallization and filtration, and concurrently forming a mother liquor substream;
   (b) dewatering said mother liquor substream;
   (c) concentrating the dewatered mother liquor substream by means of distillation;
   (d) extracting an adduct of bisphenol A and phenol from the concentrated and dewatered mother liquor substream by means of crystallization at a temperature of 40 to 50° C. at a residence time of one to six hours;
   (e) isolating the adduct of bisphenol A and phenol by means of filtration, and concurrently forming a remaining liquid mixture;
   (f) rendering the remaining liquid mixture free of oxygen, thereby forming said mixture; and (g) placing said mixture into a container,
wherein said mixture comprises,
  35 to 75 wt. % of p,p-bisphenol A,
  5 to 25 wt. % of o,p-bisphenol A, and
  20 to 50 wt. % of secondary products which are produced during the
  preparation of bisphenol A,
  wherein the sum of the percentages by weight of p,p-bisphenol A and o,p-bisphenol A is 50 to 80 wt. % and wherein the sum of the percentages by weight of p,p-bisphenol A and o,p-bisphenol A and the secondary products totals 100 wt. %.

4. The process of claim 1 further comprising separating phenol from said dewatering said mother liquor substream of step (b) prior to rendering said mother liquor substream free of oxygen in step (c).

5. The process of claim 3 further comprising separating phenol from said remaining liquid mixture of step (e), prior to rendering the remaining liquid mixture free of oxygen in step (f).

* * * * *